US005280429A

United States Patent [19]
Withers

[11] Patent Number: 5,280,429
[45] Date of Patent: Jan. 18, 1994

[54] METHOD AND APPARATUS FOR DISPLAYING MULTI-FREQUENCY BIO-IMPEDANCE

[75] Inventor: Paul O. Withers, San Diego, Calif.

[73] Assignee: Xitron Technologies, San Diego, Calif.

[21] Appl. No.: 693,364

[22] Filed: Apr. 30, 1991

[51] Int. Cl.$^5$ .............................................. G06F 15/42
[52] U.S. Cl. ........................... 364/413.15; 364/413.13; 364/413.14; 364/413.16
[58] Field of Search ...................... 364/413.15, 413.16, 364/413.13, 413.14

[56] References Cited

U.S. PATENT DOCUMENTS

| | | | |
|---|---|---|---|
| 3,316,896 | 5/1967 | Thomasset | 128/2.1 |
| 4,008,712 | 2/1977 | Nyboer | 128/2.12 |
| 4,450,527 | 5/1984 | Sramek | 364/415 |
| 4,793,362 | 12/1988 | Tedner | 128/734 |
| 4,895,163 | 1/1990 | Libke et al. | 128/734 |
| 4,911,175 | 3/1990 | Shizgal | 128/734 |
| 4,942,880 | 7/1990 | Slovak | 128/734 |
| 4,951,682 | 8/1990 | Petre | 128/713 |
| 5,063,937 | 11/1991 | Ezenwa et al. | 128/723 |

OTHER PUBLICATIONS

"Electrical Measurement of Fluid Distribution in Legs and Arms", Kanai et al., *Medical Progress through Tech.*, 12:159–170, 1987.
Equipment Using An Impedance Technique For Automatic Recording Of Fluid-Volume Changes During Hemodialysis—Med. and Bio. Eng. and Comput. 21:285–290, 1983, Tedner, B.T.
Body Composition Measurements From Whoel Body Resistance And Reactance—Surgical Forum, 36:43–44, 1986, McDougal D., et al.
Estimation Of Body Fluid Volumes Using Tetrapolar Bioelectrical Impedance Measuremetns, Avait. Envirom. Med. Dec., pp. 1163–1169, 1988, Lukaski, H. C., et al.
Fat-Free Mass Estimation By Two Electrode Impedance Method, M. G. Clin. Nutr. 52:581-5, 1990, Boulier, A., et al.
A Computer-Based Biolectric Impedance Spectroscopic System For Noninvasive Assessment of Compartmental Fluid Redistribution, Proc. Third Annual IEEE Sumposium on Computer-Based Medical Systems, Jun. 3–6, 1990, pp. 446–453, Gerth, W. A. et al.

Primary Examiner—Donald E. McElheny, Jr.
Assistant Examiner—Gita D. Shingala
Attorney, Agent, or Firm—Brown, Martin, Haller & McClain

[57] ABSTRACT

A method and apparatus for displaying complex impedance and related physical characteristics of an object at a plurality of sinusoidal frequencies over a wide frequency range. Excitation signal waveforms are stored in digital form. Digital sampling and processing circuitry provide high noise immunity and accurate measurement at all impedance phase angles. The technique is particularly well-suited to the measurement of complex impedances in living biological tissue because the digital implementation results in highly accurate measurement values over a plurality of selectable frequencies within a wide sinusoidal frequency region. A novel adaptation of digital cross-correlation and convolution techniques is used to simultaneously display real and imaginary electrical impedance of living biological tissue at several selectable sinusoidal frequencies.

22 Claims, 3 Drawing Sheets $$\frac{1}{N}\sum_1^N I_n V_n = \text{Re}[Z]$$

$$\frac{1}{N}\sum_1^N I_{90n} V_n = \text{Im}[Z]$$

METHOD AND APPARATUS FOR DISPLAYING MULTI-FREQUENCY BIO-IMPEDANCE

BACKGROUND OF THE INVENTION

1. Field of the Invention

My invention relates generally to methods for measurement and display of complex sinusoidal impedance and, more specifically, to the display of complex sinusoidal electrical impedance in biological tissues at many frequencies.

2. Background of the Invention

The concept of a complex impedance for an object is well-known in the acoustical, electrical, and mechanical arts. An object impedance is usually defined as the ratio of a motivating excitation divided by a resulting object response at a single sinusoidal frequency, $\omega$. For example, the complex mechanical impedance, Z, of a structure can be expressed as the ratio of a sinusoidal excitation force, F, to the resulting sinusoidal velocity, V, of the structure at the point of application of the excitation force, that is:

$$Z(\omega) = F(\omega,t)/V(\omega,t)$$

The complex nature of such a driving point impedance arises from the time delay, d, of the peak sinusoidal velocity, V, with respect to the peak sinusoidal excitation force, F. This is commonly expressed in the following form:

$$Z = R + iX = \frac{F(e^{i\omega t})}{V(e^{i\omega t})(e^{-i\omega d})} = \frac{F}{V} e^{i\omega d}$$

or $$Z = \frac{F}{V}(\cos \omega d + i \sin \omega d) = \frac{F}{V} \angle \omega d$$

Where:
- $\omega$ = angular sinusoidal frequency in radians/second, and
- $\omega d$ = phase delay of V with respect to F in radians.

This concept of complex object impedance at a single sinusoidal frequency can be used to express a mechanical ratio of force to velocity, an acoustic ratio of pressure to displacement, an electrical ratio of voltage to current, a thermal ratio of temperature differential to heat flow, an electromagnetic ratio of electric field to magnetic field, and so forth as is well-known in the art.

The classical method known in the art for measuring and displaying values of complex object impedance requires the measurement of the response of the object to an applied excitation at a single sinusoidal frequency. For instance, the complex electrical impedance of an object can be determined by applying a sinusoidal voltage to the object and measuring the resultant sinusoidal current flow through the object. The electrical object impedance magnitude may then be determined as the ratio of the root-mean-square (RMS) voltage and current values and the object impedance phase angle may be determined as the delay in radians of the peak sinusoidal current with respect to the peak sinusoidal voltage. The real and imaginary components of the complex object impedance may be determined from impedance magnitude and phase angle according to:

$$\text{Resistance} = Re[Z] = R = |Z|\cos\theta, \text{ where } \theta = \omega d,$$

$$\text{Reactance} = Im[Z] = X = |Z|\sin\theta, \text{ and}$$

$$\text{Impedance} = Z = R + iX$$

A number of problems are known in the impedance measurement art that lead to errors and ambiguities when the values of complex object impedance are measured and displayed. The most significant problem arises from the requirement that the complex impedance be determined at a single sinusoidal frequency. The presence of other frequency components in the excitation and response signals lead to errors in the displayed complex impedance. Practitioners in the art have proposed analog filtering techniques and special excitation signal generation methods for minimizing the errors arising from such unwanted signal components. However, analog filter devices are subject to calibration errors, thermal drift and other problems, which introduce amplitude and phase errors in the excitation and response signals. These phase errors often become severe at high values of reactance (imaginary impedance) and can completely overwhelm the character of the complex impedance under measurement.

Other serious limitations to accurate complex impedance display are well-known in the art. High impedance magnitudes require the determination of a ratio between a large excitation signal and a very small response signal, leading to errors arising from the presence of noise in the small response signal. Practitioners propose the use of very high excitation signal amplitudes to overcome the effects of such noise, but high levels of excitation signal may damage or destroy the object to which the excitation signal is applied. This is especially problematic in cases where the object under measurement is living biological tissue.

Another problem arising from the single frequency nature of complex object impedance is the difficulty in measuring complex object impedance at several frequencies over a wide frequency range. Because signal filters are necessary to ensure sinusoidal purity, these filters must be retuned to permit impedance display at other sinusoidal frequencies. The range of frequencies over which analog filters can be retuned is very limited, often to a few octaves. Alternatively, individual signal filters can be provided for each measurement frequency, but this approach seriously limits the number of frequencies for which complex object impedance can be displayed in any particular situation.

The analog signal filtering and display components used in the art are subject to calibration drift resulting from thermal changes and variations in operating region. This problem leads to a requirement for frequent recalibration to minimize complex impedance display errors, thereby preventing the rapid and effective measurement of complex object impedance at several frequencies.

The use of balanced bridge impedance measurement techniques known in the art can overcome many of the deficiencies of the signal ratio measurement methods mentioned above. However, balanced bridge techniques require a well calibrated impedance standard and are limited in practical application to the determination and display of electrical impedances. Moreover, the standard analog bridge components are presumed to be linear with respect to signal amplitude, which is an inaccurate presumption in most applications. This presumption leads to errors in display of complex object impedance that arise with changes in excitation signal level. Finally, balanced bridge techniques are unsuitable for accurate complex impedance determination over a wide frequency range and, in fact, are often limited to a single sinusoidal calibration frequency at a single excitation signal amplitude.

Another problem well-known in the art arises from the effects of small errors in impedance phase angle at angle values approaching $\pi/2$ radians (90°). At these phase angles, the tangent function approaches infinity and extremely small errors in phase angle cause extremely high errors in one or both of the complex impedance components. A number of clever techniques have been proposed by practitioners in the art to overcome this problem, but most rely on the thermal discrimination between real and imaginary electrical power flow in a circuit and are unsuitable for use over a range of frequencies or with nonelectrical impedance measurement.

Yet another problem with classical impedance measurement and display techniques is the difficulty in simultaneously determining impedance at widely separated frequencies. This problem arises when the object under measurement experiences changes in impedance properties as a result of the application of the excitation signal. An example of this is the well-known tendency of an object to increase in temperature in response to the application of an electrical voltage. When the complex object impedance is a function of object temperature, then the measurement of complex impedance at one frequency will heat the object and create errors in the measurement of complex impedance at another frequency because of the difficulty in measuring such impedances simultaneously. One solution is to use a plurality of impedance measurement and display devices to simultaneously measure complex object impedance at a plurality of sinusoidal frequencies, but this method is cumbersome and not practical for large numbers of measurement frequencies.

These and other related difficulties with accurate display of complex object impedance are exacerbated in the situation where the object of interest is living biological tissue. The measurement and display of complex electrical impedance in biological tissue has been of interest since the late 1800's By 1921 it had been well-supported that the living cell had a well-conducting interior surrounded by a relatively impermeable, poorly conducting membrane. In 1925, Fricke reported (Fricke, H., *Mathematical Treatment of the Electrical Conductivity and Capacity of Disperse Systems*, Phys. Rev. 26:678–681, 1925) that at low frequency (LF) currents, there was little conduction through the cell because of high membrane capacitance. Thus, Fricke argued that conduction occurs primarily in the extracellular fluid (ECF) compartment and, at a sufficiently high frequency (HF), the current is shunted through the cell membrane and conducts through both the ECF and intracellular fluid (ICF).

Knowledge of biological material properties has been obtained through complex impedance measurements across various cells, suspensions, fibers, eggs and tissues. Of primary significance were the discoveries of cell membrane capacitance, the beta dispersion region, the additional regions of dispersions for cell suspensions, and Maxwell's mixture theory for analyzing the impedance measurement data.

In general, all cells and tissues may be expected to show three major dispersion regions in relation to frequencies ($\alpha$, $\beta$ and $\gamma$). Of particular interest is the central $\beta$-dispersion region, which is explained by the dielectric capacity of the cell membranes. The $\alpha$ and $\gamma$ regions are attributed to a surface conductance and to intracellular components. The $\beta$ region can be expressed in either a simple or complex equivalent circuit orientation form, where parallel resistance ($R_P$) reflects extracellular fluid ($R_{ecw}$) and the series orientation corresponds to intracellular fluid resistance ($R_{icw}$) and cell membrane capacitance ($C_M$). The equivalent circuit used in the Maxwell analysis must give the semi-circular relation (impedance and admittance loci) between the real and imaginary components of the impedance as applied frequency is varied, according to Cole (Cole, K. S., *Membrane, Ions and Impulses*, University Press, Berkeley, 1968).

An early attempt to apply this concept was made by Thomassett (Thomassett, A., *Bio-Electrical Properties of Tissues*, Lyon Med. 209:1325–1352, 1963), who measured simple impedance at high (100 kHz) and low (1 kHz) frequency currents using a two-wire technique. The high correlations of high frequency impedance to total body water (TBW) and low frequency impedance to extracellular fluid gave further support to the membrane and dispersion theories. However, Thomassett's approach did not develop into a practical clinical method.

Using a four-wire configuration, Hoffer, et al. (Hoffer, E., Meador, C., Simpson, C., *Correlation of Whole-Body Impedance with Total Body Water Volume*, J. Appl. Physio. 17, 4:531–534, 1969) reported a high correlation between measured TBW and TBW estimated by $Ht^2$/Resistance at 100 kHz. However, Hoffer, et al. reported that their high standard deviations implied that further development was necessary to make the technique a practical clinical method.

A decade later, Nyboer, et al. (Nyboer, J., Liedtke, Reid, K., Gesert, W., *Nontraumatic Electrical Detection of Total Body Water and Density in Man*, Proceedings of the VI ICEBI, 381–384, 1983) found that measurements of electrical resistance at 50 kHz, combined with subject weight, height and age, could accurately determine body density (fat and lean) in human subjects These relationships were based on the assumption that a strong relationship must exist between Fat-Free Mass (FFM) and TBW estimated by impedance because FFM tissue is consistently hydrated. Following the Nyboer, et al. work, a tremendous amount of interest arose for the impedance method.

Since the Nyboer, et al. presentation, many practitioners have sought to validate the single frequency impedance method of estimating human body composition in various populations (Lukaski, H. C., Johnson, P. E., Bolonchuk, W. W., Lykken, G. I., *Assessment of Fat-Free Mass Using Bioelectrical Impedance Measurements of the Human Body*, Am. J. Clin. Nutr., 41:810–817, 1985; Segal, K., Van Loan, M., Fitzgerald, P., Hodgdon, J. A., Van Itallie, T. B., *Lean Body Mass Estimation by Bioelectrical Impedance Analysis: a Four Site Cross-Validation Study*, Am. J. Clin. Nutr. 47:7–14, 1988; and Kushner, R., Kunigk, A., Alspaugh, M., Andronis, P., Leitch, C., Schoeller, D., *Validation of Bioelectrical-Impedance Analysis as a Measurement of Change in Body Composition in Obesity*, Am. J. Clin. Nutr. 52:219–23, 1990). Results have been mostly positive for normal subjects but the predictions of FFM have been far less precise in the clinical and abnormal population groups. Although impedance data continued to correlate highly to TBW, the underlying assumption that FFM is consistently hydrated has recently been found to be incorrect (Deurenberg, P., Westtrate, J. A., Hautvast, J., *Changes in Fat-Free Mass During Weight Loss Measured by Bioelectrical Impedance and by Densitometry*, Am. J. Clin. Nutr. 49:33-6, 1989). Furthermore, increased awareness of the usefulness of the multi-frequency measurements has led to a general belief that the single frequency method is too simplistic and limiting (Cohn, S., *How Valid are Bioelectrical Impedance Measurements in Body Composition Studies?*, Am. J. Clin. Nutr. 42:889-890, 1985). Criticism was also raised over the clinical usefulness of TBW in view of frequently encountered fluid shifts between the ICW and ECW. Van Itallie, et al. (Van Itallie, T., Segal, K., *Nutritional Assessment of Hospital Patients: New Methods and New Opportunities*, Am. J. Hum. Bio 1:205-8, 1989) assert that a practical method of discerning the ICW from the extracellular fluid would offer much greater utility and could profoundly influence hospital patient care and diagnosis.

Recently, several practitioners (Lukaski, H. C., Bolonchuck, W. W., *Estimation of Body Fluid Volumes Using Tetrapolar Bioelectrical Impedance Measurements*, Aviat. Space Environ., Med Dec., 1163-69, 1988 and McDougall, D., Shizgal, H., *Body Composition Measurements from Whole Body Resistance and Reactance*, Surgical Forum, 36:43-44, 1986) have proposed using the reactive element in a complex single frequency (50 kHz) impedance measurement to accurately discriminate the extracellular from the cellular mass. However, the use of multi-frequency measurements of impedance remains the technique of choice (Boulier, A., Fricker, J., Thomassett, A. L., Apfelbaum, M., *Fat-Free Mass Estimation by Two-Electrode Impedance Method*, Am. J. Clin. Nutr. 52:581-5, 1990).

Several practitioners have continued to test the Thomassett technique (Jenin, P., Lenoir, J., Roullet, C., Thomassett, A., Ducrot, H., *Determination of Body Fluid Compartments by Electrical Impedance Measurements*, Aviat Space Environ. Med. 46:152-5, 1975; Settle, R. G., Foster, K. R., Epstein, B. R., Mullen, J. L., *Nutritional Assessment: Whole Body Impedance and Body Fluid Compartments*, Nutr. Cancer, 2:72-80, 1980; and Tedner, B. T., *Equipment Using an Impedance Technique for Automatic Recording of Fluid-Volume Changes During Hemodialysis*, Med. & Biol. Eng. & Comput. 21:285-290, 1983). These practitioners use the ratio of high to low frequency simple impedance to reflect fluid compartment volume, the normal and abnormal fluid ratio, and fluid compartment change. The major problem reported for this technique is that the simple HF/LF ratio is too simplistic because volume is not determined and the compartment actually affected is not identified, although a change in ratio does reflect a change in compartmental volume. Furthermore, practitioners note that the lack of two-frequency simple impedance instrumentation prevents further exploration of this approach.

Because living tissue is mainly affected by ECF at frequencies below the $\beta$-dispersion region, and ECF, $C_M$ and ICF at frequencies above this region, Kanai, et al. (Kanai, H., Haeno, M., Sakamoto, K., *Electrical Measurements of Fluid Distribution of Legs and Arms*, Med. Prog. Tech. 12:159-170, 1987) Computed the component values of the human muscle tissue equivalent circuit model ($R_{ecw}$, $R_{kw}$, and $C_M$) known in the art. By mathematically analyzing the complex impedance measurements at multiple frequencies, Kanai, et al. obtained information specific to the ECW and ICW. However, others have been unable to replicate this advanced approach because of the lack of necessary and appropriate complex impedance instrumentation.

Expanding the prior art human body composition model from a simple two-compartment (lean/fat) model to a more complex model including ICF and ECF, protein, mineral and fat, creates a clearly-felt need for new and improved assessment techniques. This need has been unmet, until now because of the lack of appropriate complex impedance instrumentation and the lack of the necessary degree of sophistication in the associated measurement and analysis methods. This situation has inhibited the progress of this promising technology.

Increased use of diuretic drugs, fluid monitoring difficulties in intensive care, and the shrinking cell mass and expanding ECF that accompany most systemic wasting diseases and malnutrition has led to a well-recognized need for effective multi-frequency bioimpedance instrumentation in support of the compartmental approach to body fluid assessment. These unresolved problems and deficiencies are clearly felt in the art and are solved by my invention in the manner described below.

SUMMARY OF THE INVENTION

My invention is a method and apparatus for the simultaneous determination and display of complex electrical bio-impedance at several frequencies. Although I teach primarily the application of my invention to the display of multi-frequency electrical bio-impedance, my invention is also readily applicable to the determination and display of complex impedances for many other types of objects, including other impedances such as mechanical, acoustic and the like. This can be appreciated by recognizing that my invention determines and displays complex object impedance by treating an excitation signal and a response signal as two independent functions in the time domain. Because of this view, I can apply certain signal processing techniques to the two independent time domain signals to obtain results in a manner previously unsuspected in the art.

The first such signal processing concept that I use is the creation of a complex cross-correlation signal as a function of time delay, $\tau$, between the excitation, e, and response, r, signals. My complex cross-correlation function, $R_{er}(\tau)$, can be developed from the integral over time of the product of the two excitation and response signals where the response signal is delayed by time $\tau$ with respect to the excitation signal.

The second signal processing concept that I use is the complex Fourier transform, F, of the cross-correlation signal, $R_{er}(\tau)$. The Fourier transform of $R_{er}(\tau)$ is $F(R_{er})$, which is a signal in the frequency domain having a complex value at each angular frequency $\omega$ that is proportional to the complex object impedance.

Following the conversion of the two excitation and response signals to an intermediate cross-correlation signal and a final Fourier transform signal, I display the complex object impedance as a function of frequency over a predetermined range. My cross-correlation signal and Fourier transform signals are both complex because they exhibit amplitude and phase information at each point in the time delay and frequency domains, respectively.

My application of these simple signal processing techniques for the conversion of time domain signals to frequency domain signals can be embodied in a an apparatus using either analog or digital electronic components. An advantage of my preferred embodiment is that my use of digital components leads to improved storage and processing accuracy and minimizes the effects of analog component calibration drift. I have also discovered that the development of a complete cross-correlation signal, $R(\tau)$, over a large time-delay region and the subsequent development of a Fourier transform signal, $F(\omega)$, over a broad frequency region, while possible, is not the most useful embodiment of my invention. Accordingly, I have refined this elementary convolution approach by adding the following improvements.

First, I use an electrical current for the excitation signal instead of the electrical voltage normally used in the art. The constant current excitation signal prevents unsuspected hazards to living biological tissues because the biological hazards are more closely related to current levels than to voltage levels as is known in the medical art. Secondly, I make use of a series of stored digital data to define the excitation current waveform precisely. By precisely defining the excitation current waveform, I can create and apply a single-frequency excitation current to the living biological object under measurement. Conversion of two such single-frequency excitation and response signals to a cross-correlation signal results in a sinusoidal cross-correlation signal having an amplitude and phase representative of the complex cross-correlation between the excitation and response signal. Moreover, the Fourier transform of such a sinusoidal cross-correlation signal is a single impulse function at the point in the frequency domain equivalent to the single frequency of the initial excitation and response signal.

These observations are particularly useful because they result in simplification of my signal and convolution conversion process to a simple signal multiplication procedure in quadrature. That is, the complex object impedance at a single frequency can be developed from the excitation and response signals in the time domain by a multiplication and integration process in quadrature. This quadrature signal conversion method is the preferred embodiment of my invention because of the relatively simple apparatus necessary.

A potential problem with my quadrature technique is that a different excitation waveform is required for each sinusoidal frequency value at which complex object impedance must be displayed. I have resolved this problem by providing for the storage of a plurality of excitation waveforms in a signal generator digital memory means so that the excitation signal can be quickly stepped through a variety of sinusoidal frequencies merely by selecting the necessary waveform data from the memory device in the desired sequence. The excitation current is then produced from the stored digital data and the analog response voltage developed across the object under measurement is sensed. Moreover, network analyzer means may be added to compute and display a plurality of equivalent circuit elements from a similar plurality of complex impedance data obtained at the different sinusoidal frequencies stored in my digital signal generator memory means.

For ease of implementation and minimization of measurement and display errors, I prefer to perform all signal conversions using digital means. Accordingly, in my preferred embodiment, the response and excitation signals are converted to digital form by sampling means and the multiplication of the two excitation response signals in the time domain is performed using digital multiplication means. The real or resistive component of the complex object impedance is related to a first impedance signal expressed as the arithmetic average of the products of a series of simultaneous samples of the excitation signal and response signal. The imaginary or reactive component of the complex object impedance is related to a second impedance signal, expressed as the arithmetic average of a series of products of simultaneous samples of the response signal and a delayed excitation signal, where the delay is precisely equal to $\pi/2$ radians or one-fourth cycle of the sinusoidal waveform representing the frequency at which the complex object impedance is determined.

By using digital sampling techniques and synchronizing the sampling windows of the excitation and response signals, the implementation of my preferred embodiment is simplified and the signal conversion process made more robust (resistant to noise and calibration errors). It is not necessary to independently sample the excitation current waveform because this waveform is developed from digital samples stored in a digital memory device and these samples can be used directly in the quadrature multiplication process. However, I prefer to independently sample the analog excitation current waveform at the point where it is applied to the biological object for two reasons. First, this simplifies the synchronization of the sampling windows for the two excitation and response signals. Secondly, this avoids errors arising from unexpected changes in the excitation signal between the memory storage means and the point of application to the object under measurement.

One of the advantages of my invention is that complex bio-impedance can be measured almost simultaneously at a plurality of frequencies in a wide frequency region. Another advantage of my invention is that a change in the sinusoidal excitation signal frequency can be achieved without changing analog circuit paths or component values. This minimizes the errors arising from component calibration errors. An objective of my invention is to avoid complex impedance errors arising from nonlinearities in the object under measurement. Yet another advantage of my invention is the rejection of noise effects over a broad frequency range without the use of analog filter techniques. It is another object of my invention to accurately display the complex object impedance phase at all phase values from $-90°$ to $+90°$. Another advantage of my invention is that a variety of calibration factors may be readily applied to the displayed results by using digital techniques known in the art.

An important objective of my invention is to permit the measurement of bio-impedance at a plurality of frequencies in as little as two cycles of the primary frequency waveform. Another important advantage of my invention is that my time series convolution process eliminates most errors that otherwise arise from the undesired presence of random noise in the relevant signals.

The foregoing, together with other features and advantages of my invention will become more apparent when referring to the following specifications, claims and the accompanying drawings.

BRIEF DESCRIPTION OF THE DRAWINGS

For a more complete understanding of my invention, reference is now made to the following detailed description of the embodiments illustrated in the accompanying drawings wherein:

FIG. 1, comprising

FIGS. 2A and 2B, illustrates a method for applying an excitation signal to an object and detecting a resulting response signal and shows a typical equivalent circuit representation of a living cell;

DESCRIPTION OF THE PREFERRED EMBODIMENT

Figure 1A:
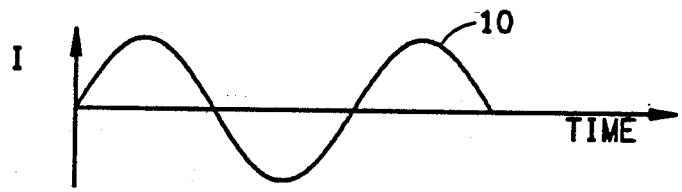
FIGS. 1(a) through 1(h), shows a series of waveforms in the time domain exemplifying the excitation signal, delayed excitation signal, response signal, first and second impedance signals and the related series of digital samples.
Figure 1B:
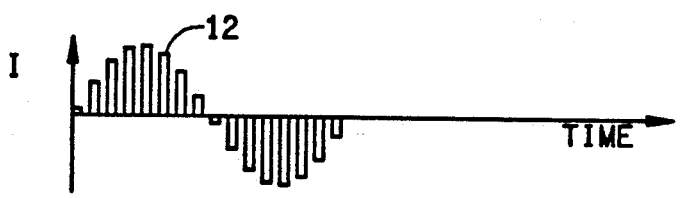
Figure 1C:
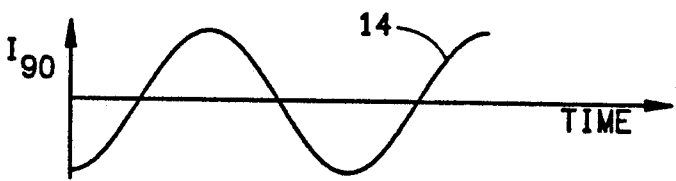
Figure 1D:
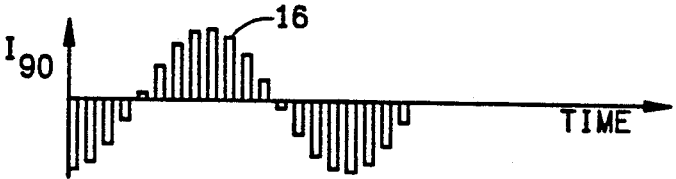

FIG. 1 illustrates the typical waveform characteristics for the excitation and response signals used in my invention for displaying complex object impedance. FIG. 1A shows an excitation signal current 10 that varies in amplitude sinusoidally with time in the manner shown. FIG. 1B shows the resulting series of excitation pulses or samples 12 that represent current 10 samples made at a predetermined sampling rate. This predetermined sampling rate should be high enough (as seen from the Nyquist criteria, known in the art) to avoid losing significant phase and amplitude information contained in current 10. FIG. 1C illustrates a delayed excitation signal current 14 that is identical to current 10 except for a time delay of $\pi/2$ radians or one-quarter cycle of the sinusoidal waveform. FIG. 1D illustrates a series of delayed excitation pulses or samples 16 that represent current waveform 14 samples taken in synchronism with excitation current samples 12.

Figure 1E:
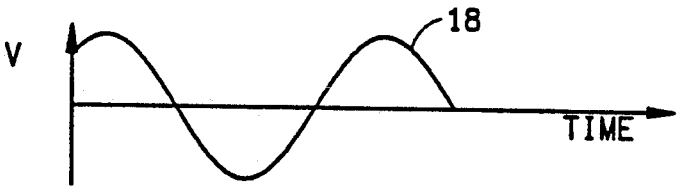
Figure 1F:
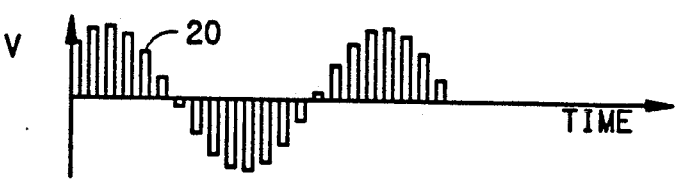

In operation, my invention uses excitation signal current 10 to excite a living biological tissue sample and I then monitor the sample for a response signal voltage waveform 18 shown in FIG. 1E. Response signal voltage 18 may contain several sinusoidal frequency components, but the fundamental sinusoidal frequency of signal current 10 will predominate. FIG. 1F illustrates a series of response voltage samples 20 that are taken in synchronism with samples 12 and 16.

Figure 1G:
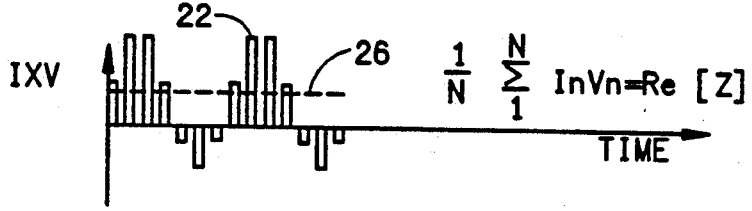
Figure 1H:
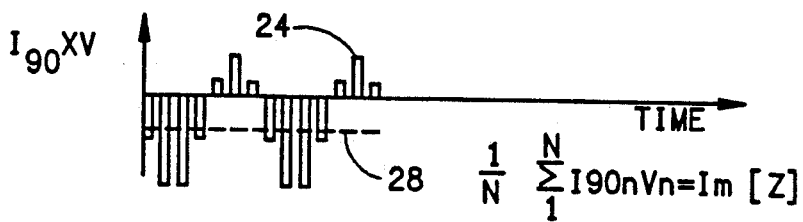

FIGS. 1G and 1H illustrate the first impedance samples 22 and second impedance samples 24, respectively. Sample 22 is obtained by multiplying the concurrent values of sample 12 and sample 16 ($I_nV_n$), either by analog or digital means. Sample 24 is obtained by multiplying concurrent values of delayed excitation sample 16 and response voltage sample 20 ($I_{90n}V_n$). FIG. 1G shows a first mean impedance signal 26 representing the long term arithmetic average of impedance samples 22. Similarly, FIG. 1H shows a second mean impedance signal 28 representing the long term arithmetic average of samples 24.

Figure 2:
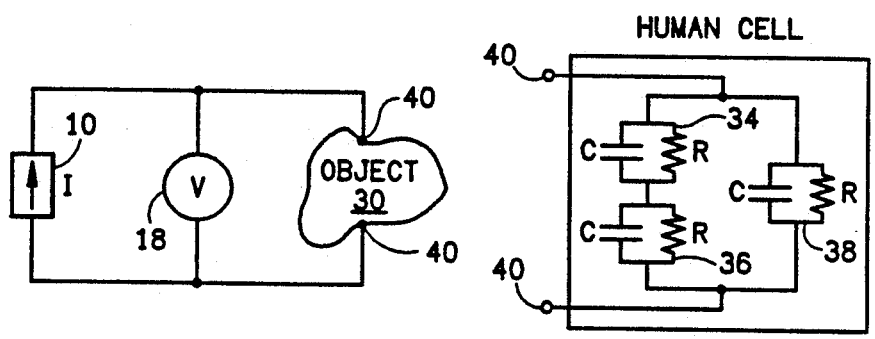
FIG. 2, comprising

While I believe that my invention is useful for determining many different types of impedances, including thermal, mechanical, acoustical and so forth, I limit my discussion herein to my preferred application, which is the measuring of complex electrical impedances of living biological tissues. FIG. 2A illustrates the fundamental arrangement required to measure and display complex electrical impedance of an object 30. Excitation signal current 10 is applied to object 30 and response signal voltage 18 is monitored.

FIG. 2B illustrates a useful equivalent circuit model for the living human cell 32 proposed by Kanai, et al., cited above. Cell model 32 comprises three lumped constant RC circuits 34, 36 and 38. RC circuit 34 represents the cell membrane capacitance and cell membrane resistance. RC circuit 36 represents the intracellular fluid capacitance and resistance. RC circuit 38 represents the extracellular fluid capacitance and resistance.

Human cell equivalent circuit 32 presents a single complex impedance to the pair of terminals 40 at any single sinusoidal frequency. Accordingly, the six lumped-constant model elements can be determined only from impedance data at six (or more) different sinusoidal frequencies by means of a critically-or over-determined system of linear equations as known in the art.

Figure 3:
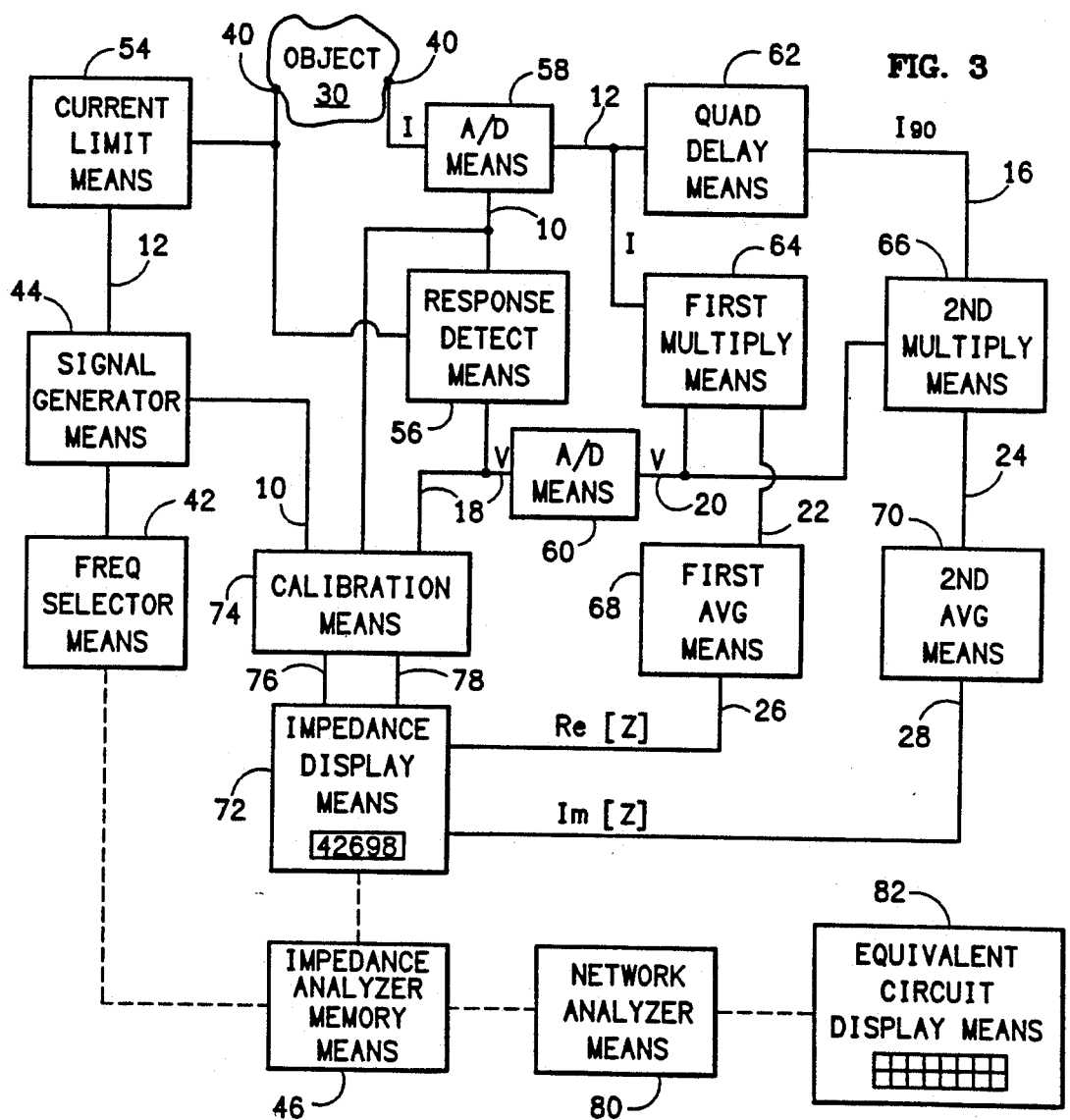
FIG. 3 is an illustrated embodiment of an apparatus for measuring and displaying the complex impedance of an object.

As discussed above, I prefer to use a simplified signal multiplication procedure in quadrature to determine complex object impedance. This signal multiplication procedure was introduced and described in connection with FIG. 1, wherein first and second mean impedance signals 26 and 28 represent real and imaginary components (Re[Z],Im[Z]). FIG. 3 shows a functional implementation of my invention, including the necessary means for determining a plurality of equivalent circuit element values such as described in FIG. 2B for human cell 32. These equivalent circuit analyzer elements are shown connected by dotted lines in FIG. 3, and are further described below.

Figure 4:
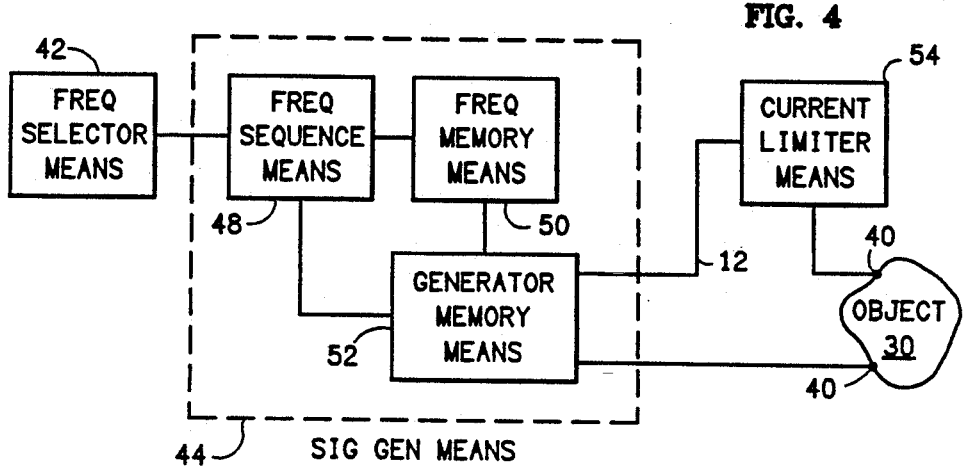
FIG. 4 is an illustrated embodiment of the signal generating means from FIG. 3.

A frequency selecton means 42 may comprise front panel switch controls, digital memory means or other related devices suitable for selecting one or more sinusoidal operating frequencies. Each selected frequency is passed to a signal generator means 44 and also to an impedance analyzer memory means 46. Impedance analyzer memory means 46 merely receives the frequency selection and stores it in memory for later use with concurrent complex body impedance data. Signal generator means 44 preferably comprises a frequency sequencing means 48, a frequency memory means 50 and a generator memory means 52 as shown in FIG. 4. Frequency sequencing means 48 selects from among a plurality of operating frequencies stored in memory means 50 and 52. Frequency memory means 50 provides the necessary clocking pulses to generator memory means 52, which then provides a train of excitation current pulses making up a sinusoidal excitation current in response to the commands received from frequency sequencing means 48 and frequency memory means 50.

Returning to FIG. 3, a current limiting means 54 is interposed in series with excitation current samples 12 to prevent the excitation current amplitude from exceeding biologically safe levels. Excitation current samples 12 are then imposed on object 30 at terminals 40 and a response detector means 56 is connected across terminals 40 to measure response signal voltage 18.

First and second analog-to-digital (A/D) conversion means 58 and 60 serve to convert excitation signal current 10 and response signal voltage 18 from analog form to digital form in a manner known in the art. The operation of A/D means 58 and 60 is synchronized with the operation of signal generator means 44 by clocking means (not shown) to ensure that the leading and lagging edges of the digital pulses created by the three circuits are synchronous in time to within less than one microsecond.

The output of first A/D means 58 presents excitation samples 12 to the input of a quadrature delay means 62 and the first input of a first multiplier means 64. The output of second A/D means 60 presents response samples 20 to the second input of first multiplier means 64 and the first input of a second multiplier means 66. The output of quadrature delay means 62 provides delayed excitation samples 16 that represent a digital embodiment of delayed excitation signal current 14 discussed in connection with FIG. 1. Delayed excitation signal current 14 lags excitation signal current 10 by precisely one-fourth of a waveform cycle at the fundamental sinusoidal operating frequency. Delayed excitation samples 16 from quadrature delay means 62 are presented to the second input of second multiplier means 66.

The output of first multiplier means 64 provides a series of pulses equal to the series of products of concurrent excitation samples 12 and response samples 20, which we have named first impedance samples 22 in FIG. 1. Similarly, the output of second multiplier means 66 provides a series of pulses named second impedance samples 24, which is the series of products of concurrent delayed excitation samples 16 and response samples 20. First impedance samples 22 are presented to a first averaging means 68 and second impedance samples 24 are presented to a second averaging means 70. The outputs from first and second averaging means 68 and 70 comprise first and second mean impedance signals 26 and 28 as discussed above in connection with FIG. 1. Signals 26 and 28 are exactly proportional to the real and imaginary components of the complex electrical impedance of object 30. Signals 26 and 28 are presented to impedance display means 72, which is preferably a multi-digit LCD numerical display or other suitable display means known in the art.

The calibration means 74 comprises circuitry that produces a current calibration signal 76 and a voltage calibration signal 78 for use in adjusting impedance display means 72 in response to independent calibration of excitation signal current 10 and response signal Voltage 18.

Impedance display means 72 also presents the complex impedance of object 30 to impedance analyzer memory means 36 for storage together with the relevant sinusoidal frequency value presented by signal frequency selection means 42. These data are stored in impedance analyzer memory means 46 for use in computing a plurality of lumped constant equivalent circuit elements as discussed above in connection with FIG. 2. These equivalent circuit elements are computed and displayed by means of a network analyzer means 80 and an equivalent circuit display means 82 disposed substantially as shown in FIG. 3. Network analyzer means 80 acts to solve a system of linear equations for a plurality of equivalent circuit elements from a plurality of complex impedance and operating frequency data pairs in any suitable digital or analog manner known in the art for solving linear systems of equations. The resulting equivalent circuit element values are then presented by network analyzer means 80 to equivalent circuit display means 82 for display in any suitable manner known in the art for displaying data.

Figure 5:
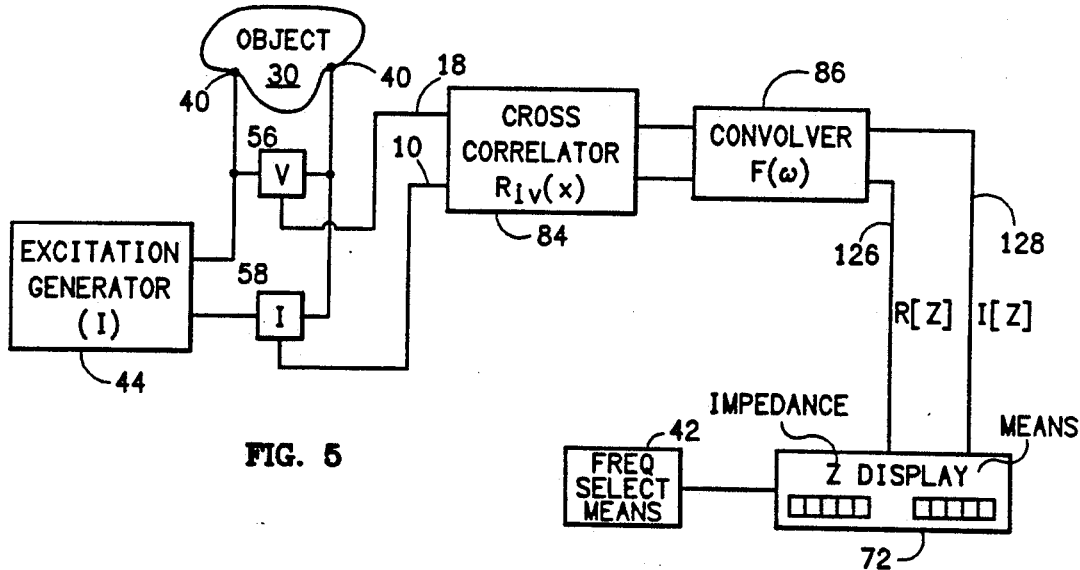
FIG. 5 is an illustrated embodiment of an apparatus that uses my more general convolution method to display the complex impedance of an object over a region in the frequency domain.

Although I prefer the simple digital quadrature multiplication and integration process discussed above, I also show in FIG. 5 the use of a cross-correlator means 84 and a convolver means 86 accomplish a similar result in lieu of the apparatus disclosed in FIG. 3. The effect of cross-correlation of signals 18 and 10 followed by convolution of the cross-correlation function $R_{iv}(\tau)$ shown in FIG. 5 was briefly discussed above and is further treated in detail by K. G. Beauschamp and C. Yuen, *Digital Methods for Signal Analysis*, George Allen & Unwin, Ltd, London, 1979. The applications of these digital signal processing techniques to the measurement of complex body impedance is suggested herein for the first time. Note that the two outputs 126 and 128 from convolver 86 contain complex impedance data over the entire frequency domain and impedance display means 72 can be configured to display impedance data at a single frequency in response to an input from frequency selection means 42.

Obviously, other embodiments and modifications of my invention will occur readily to those of ordinary skill in the art in view of these teachings. Therefore, my invention is to be limited only by the following claims which include all such obvious embodiments and modifications when viewed in conjunction with the above specification and accompanying drawings.

I claim:

1. A method for detecting the complex impedance of biological tissue at a sinusoidal frequency comprising the steps of:
   selecting a sinusoidal frequency value;
   selecting a first sampling rate no less than 400% of said sinusoidal frequency;
   selecting a second sampling rate no less than first said sampling rate;
   generating a series of excitation pulses at said first sampling rate to form an excitation signal comprising a component at said sinusoidal frequency having a predetermined magnitude;
   spanning said biological tissue with at least one pair of electrically conductive terminals;
   applying said excitation signal across said at least one pair of terminals to said biological tissue;
   detecting a response signal comprising the response of said biological tissue to said applied excitation signal;
   sampling said excitation signal at said second sampling rate to form a series of excitation samples;
   sampling said response signal at said second sampling rate in synchronism with said excitational sampling step to form a series of response samples;
   delaying said excitation samples by a delay time substantially equal to one-fourth cycle of said sinusoidal frequency to form a series of delayed excitation samples;
   multiplying each said excitation sample by the simultaneous said response sample to form a first impedance sample;
   multiplying each said delayed excitation sample by the simultaneous said response sample to form a second impedance sample;
   averaging said first and second impedance samples over time to form first and second mean impedance signals, respectively; and
   providing an output comprising said first and second means impedance signals representative of the complex impedance of said biological tissue.

2. The method described in claim 1 wherein:
   the complex impedance comprises the electrical impedance of said object; and said sinusoidal excitation signal comprises an electrical current of substantially invariant sinusoidal magnitude.

3. The method described in claim 2 wherein:
said first sampling rate is equal to said second sampling rate and said first and second sampling steps are synchronized with said generating step.

4. A method for determining the complex impedance of biological tissue over a range of sinusoidal frequencies comprising the steps of:
 selecting a first sampling of no less than 400% of the maximum said sinusoidal frequency;
 selecting a second sampling rate no less than said first sampling rate;
 generating a series of excitation pulses at said first sampling rate to form an excitation signal;
 spanning said biological tissue with at least one pair of terminals;
 applying said excitation signal to said at least one pair of terminals across said biological tissue;
 detecting a response signal comprising the response of said biological tissue to said applied excitation signal;
 sampling said excitation signal and said response signal in synchronism at said second sampling rate to form a series of synchronous excitation samples and response samples, respectively;
 computing the complex cross-correlation of said series of excitation samples and said series of response samples over a predetermined time delay region;
 computing the real and imaginary components of the Fourier transform of said complex cross-correlation over said range of sinusoidal frequencies to form first and second impedance signals, respectively;
 computing the square of the magnitude of the Fourier transform of said excitation signal over said range of sinusoidal frequencies to form a calibration signal;
 displaying the ratios of said first and second impedance signals to said calibration signal to represent said complex impedance of said biological tissue over said range of sinusoidal frequency.

5. The method described in claim 4 wherein:
said first sampling rate is equal to said second sampling rate and said first and second sampling steps are synchronized with said generating step.

6. An apparatus for measuring and displaying the complex impedance of biological tissue comprising:
 at least one pair of terminals disposed in electrical communication with said biological tissue;
 frequency selection means for selecting at least one sinusoidal frequency;
 signal generating means for creating an excitation signal across said at least one pair of terminals, said excitation signal having a sinusoidal component at said selected sinusoidal frequency;
 response detection means for detecting a response signal arising in said biological tissue across said at least one pair of terminals in response to application of said excitation signal;
 quadrature delay means for delaying said excitation signal by a predetermined time period to create a delayed excitation signal;
 first multiplier means for multiplying said excitation signal and response signal to form a first impedance signal;
 second multiplier means for multiplying said delayed excitation signal and response signal to form a second impedance signal;
 fist averaging means for averaging said first impedance signal over time to form a first mean impedance signal;
 second averaging means for averaging said second impedance signal over time to form a second mean impedance signal; and
 display means for displaying said first and second mean impedance signals to represent said complex impedance of said biological tissue at said selected sinusoidal frequency.

7. The apparatus described in claim 6 further comprising:
 frequency memory means for storing a plurality of selected sinusoidal frequencies; and
 frequency sequencing means for stepping through said plurality of sinusoidal frequencies and sequentially displaying said complex impedance of said biological tissue for each said sinusoidal frequency in turn.

8. The apparatus described in claim 7 further comprising:
 calibration means for adjusting said first and second mean impedance signals in accordance with variations in excitation signal magnitude.

9. The apparatus described in claim 6 wherein:
said sinusoidal frequency generating means, said response detection means, said delay means and said first and second multiplier means comprise digital electronic logic means.

10. The apparatus described in claim 9 wherein:
said display means comprises digital display means for displaying numerical values of said complex impedance of said biological tissue.

11. The apparatus described in claim 9 further comprising:
 frequency memory means for storing a plurality of selected sinusoidal frequencies; and
 frequency sequencing means for stepping through said plurality of sinusoidal frequencies and sequentially displaying said complex impedance of said biological tissue for each said sinusoidal frequency in turn.

12. The apparatus described in claim 11 further comprising:
 generator memory means for storing a plurality of digital words representing said excitation signal; and
 digital-to-analog conversion means for converting said digital words to an analog excitation signal.

13. The apparatus described in claim 12 wherein:
said response detection means comprises analog-to-digital conversion means for sampling said response signal to form a series of response samples.

14. The apparatus described in claim 13 wherein:
said excitation signal comprises a sinusoidal electrical current and said response signal comprises a sinusoidal electrical voltage.

15. The apparatus described in claim 6 further comprising:
 current limiting means for limiting said excitation signal current to a value that will cause no harm when applied to said biological tissue.

16. An apparatus for measuring and displaying at least one equivalent circuit component arising from a theoretical model of biological tissue comprising:

at least one pair of terminals for spanning said biological tissue;

frequency selection means for selecting at least one sinusoidal frequency;

signal generating means for creating an excitation signal comprising a sinusoidal component at said selected sinusoidal frequency for conduction across said at least one pair of terminals;

response detection means electrically connected to said at least one pair of terminals for detecting a response signal arising in said biological tissue in response to application of said excitation signal;

quadrature delay means for delaying said excitation signal by a predetermined time period to create a delayed excitation signal;

first multiplier means for multiplying said excitation signal and response signal to form a first impedance signal;

second multiplier means for multiplying said delayed excitation signal and response signal to form a second impedance signal;

first averaging means for averaging said first impedance signal over time to form a first mean impedance signal;

second averaging means for averaging said second impedance signal over time to form a second mean impedance signal;

first memory means for storing said first and second mean impedance signals to represent said biological signal impedance at said selected sinusoidal frequency;

processing means for obtaining a plurality of said first and second mean impedance signals representing said biological tissue impedance at a plurality of selected sinusoidal frequencies;

network analyzer means for inverting said plurality of biological tissue impedances to a plurality of equivalent circuit element values; and display means for displaying said plurality of biological tissue equivalent circuit values.

17. An apparatus for assessing the composition of biological tissue comprising:

a wave generator for generating a signal at at least one sinusoidal frequency;

a signal generator responsive to said wave generator for generating an excitation signal at said at least one sinusoidal frequency;

at least one pair of terminals for spanning said biological tissue and applying said excitation signal thereof;

a detector for detecting a response signal arising in said biological tissue in response to application of said excitation signal;

delay means for delaying said excitation signal by a predetermined time period to create a delayed excitation signal;

first multiplier means for multiplying said excitation signal and response signal to form a fist impedance signal;

second multiplier means for multiplying said delayed excitation signal and response signal to form a second impedance signal;

first averaging means for averaging said first impedance signal over time to generate a first mean bio-impedance signal;

second averaging means for averaging said second impedance signal over time to generate a second mean bio-impedance signal; and an output means for providing said first and second mean impedance signals which represent a complex bio-impedance of said biological tissue at said at least one sinusoidal frequency, wherein said complex bio-impedance is representative of composition of said biological tissue.

18. An apparatus for assessing the composition of biological tissue as in claim 17 further comprising:

frequency memory means for storing a plurality of selected sinusoidal frequencies; and sequencing means for stepping through said plurality of selected sinusoidal frequencies and sequentially outputting said complex bio-impedance corresponding to each selected sinusoidal frequency.

19. An apparatus for assessing the composition of biological tissue as in claim 17 further comprising:

calibration means for varying said first and second means impedance signals in accordance with variations in excitation signal magnitude.

20. An apparatus for assessing the composition of biological tissue as in claim 17 wherein said wave generator, said response detector, said delay means and said first and second multiplier means are all digital.

21. An apparatus for assessing the composition of biological tissue as in claim 20 further comprising:

generator memory means for storing a plurality of digital words representative of said excitation signal; and digital-to-analog conversion means for converting said digital words into an analog excitation signal.

22. An apparatus for assessing the composition of biological tissue as in claim 17 further comprising:

current limiting means for limiting electrical current within said excitation signal to avoid harming said biological tissue.

* * * * *